(12) United States Patent
Orecchia

(10) Patent No.: US 6,790,037 B1
(45) Date of Patent: Sep. 14, 2004

(54) DENTAL VISCOUS MATERIAL DISPENSER WITH CAPULE LOCK

(75) Inventor: Mike Orecchia, Westminster, CO (US)

(73) Assignee: Confi-Dental Products Co., Louisville, CO (US)

( * ) Notice: Subject to any disclaimer, the term of this patent is extended or adjusted under 35 U.S.C. 154(b) by 0 days.

(21) Appl. No.: 10/608,557

(22) Filed: Jun. 30, 2003

(51) Int. Cl.[7] .............................................. A61C 5/04
(52) U.S. Cl. ...................................................... 433/90
(58) Field of Search ..................... 433/89, 90; 222/325, 222/326, 327, 567; 604/239

(56) References Cited

U.S. PATENT DOCUMENTS

| | | | |
|---|---|---|---|
| 2,648,906 A | | 8/1953 | Holmes |
| 2,837,824 A | | 6/1958 | Moller |
| 3,581,399 A | | 6/1971 | Dragan |
| 4,198,756 A | | 4/1980 | Dragan |
| 4,295,828 A | | 10/1981 | Rudler |
| 4,330,280 A | | 5/1982 | Dougherty et al. |
| 4,384,853 A | | 5/1983 | Welsh |
| 4,431,414 A | * | 2/1984 | Lawrence ..................... 433/90 |
| 4,472,141 A | | 9/1984 | Dragan |
| 4,813,871 A | | 3/1989 | Friedman |
| D315,956 S | | 4/1991 | Dragan |
| 5,061,179 A | | 10/1991 | Dragan |
| 5,125,836 A | | 6/1992 | Dragan et al. |
| 5,165,890 A | | 11/1992 | Discko, Jr. |
| 5,172,807 A | | 12/1992 | Dragan et al. |
| D334,803 S | | 4/1993 | Discko, Jr. |
| 5,267,859 A | | 12/1993 | Discko, Jr. |
| 5,306,147 A | | 4/1994 | Dragan et al. |
| 5,336,088 A | | 8/1994 | Discko, Jr. |
| D353,673 S | | 12/1994 | Discko, Jr. et al. |
| D357,536 S | | 4/1995 | Dragan et al. |
| D359,119 S | | 6/1995 | Dragan et al. |
| D359,560 S | | 6/1995 | Mitchell |
| 5,489,207 A | | 2/1996 | Dragan et al. |
| 5,707,234 A | | 1/1998 | Bender |
| 5,871,355 A | | 2/1999 | Dragan et al. |
| 6,047,864 A | * | 4/2000 | Winkler ..................... 222/326 |
| 6,059,570 A | | 5/2000 | Dragan et al. |
| 6,099,307 A | | 8/2000 | Discko, Jr. |
| 6,116,414 A | | 9/2000 | Discko, Jr. |
| 6,116,902 A | * | 9/2000 | Schodel et al. ............... 433/89 |
| 6,135,771 A | | 10/2000 | Dragan et al. |
| D435,292 S | | 12/2000 | Dragan et al. |
| 6,379,152 B1 | | 4/2002 | Dragan |
| D460,822 S | | 7/2002 | Dragan et al. |
| 6,422,866 B2 | | 7/2002 | Dragan et al. |
| D461,247 S | | 8/2002 | Dragan et al. |

* cited by examiner

*Primary Examiner*—Cary E. O'Connor
(74) *Attorney, Agent, or Firm*—Arent Fox, PLLC

(57) ABSTRACT

A viscous material dispenser for applying a viscous dental material from a capule, cartridge or capsule. The dispenser includes a locking mechanism mounted on the syringe type dispenser to securely retain the capule, cartridge or capsule within the syringe type dispenser while the viscous material is being applied from the syringe type dispenser. The locking mechanism can be positioned so that it rotates around and over the outer circumference of the dispensing barrel of the syringe type dispenser. The locking mechanism can be rotated to an open position where a capule, capsule or cartridge can be inserted or removed from the syringe type dispenser. After a capule, cartridge or capsule is inserted within the syringe barrel, the locking mechanism can be rotated to a closed position where the capule, cartridge or capsule is locked and retained in place for dispensing.

16 Claims, 6 Drawing Sheets

DENTAL VISCOUS MATERIAL DISPENSER WITH CAPULE LOCK

BACKGROUND OF THE INVENTION

1. Field of the Invention

This invention is related to a viscous material dispenser, and particularly to a multiple use dental syringe adapted to lock in place a viscous material capule.

2. Description of the Related Art

Various dispensing devices for dispensing viscous dental compositions and the like are known in the art, such as, for example, disclosed in U.S. Pat. Nos. 6,422,866; 6,379,152; 6,135,771; 6,116,414; 6,099,307; 6,059,570; 5,871,355; 5,707,234; 5,489,207; 5,336,088; 5,306,147; 5,267,859; 5,172,807; 5,165,890; 5,125,836; 5,061,179; 4,813,871; 4,619,613; 4,492,576; 4,472,141; 4,384,853; 4,330,280; 4,315,743; 4,295,828; 4,198,756; 4,084,320; 3,828,434; 3,760,503; 3,618,216; 3,581,399; 3,436,828; 3,346,147; 2,903,794; 2,837,824; 2,648,906; 683,075; Des. 461,247; Des. 460,822; Des. 435,292; Des. 359,560; Des. 357,141; Des. 359,119; Des. 357,536; Des. 353,673; Des. 334,803; and Des. 315,956; the subject matter of all of which are incorporated herein by reference in their entireties.

FIG. 1 is a view of a conventional syringe 30' for dispensing viscous dental compositions, in conjunction with a capule 40 or the like, taken from U.S. Des. 359,560 to Mitchell, the subject matter of which is incorporated herein by reference in its entirety.

The front end portion of the syringe 30' extends only partially around the circumference of the barrel. An opening for inserting a capule or the like is thus formed where the front end circumferential portion of the barrel is absent. A slot for supporting a capule or the like is also formed by the partial inside circumference of the front end portion of the syringe.

The capule 40 can be inserted into the syringe 30' through the opening and mounted in the slot thus formed. The capule 40 can similarly be removed from the syringe 30' out of the slot and through the opening.

When positioned in the slot, the capule 40 is supported by the front end portion that extends partially around the circumference of the barrel. The capule is not supported where the opening is formed where the front end circumferential portion of the barrel is absent.

In U.S. Pat. No. 4,384,853 to Welsh, a dental syringe having a snap-fit front end barrel construction is disclosed. In the snap-fit type construction, a lower portion of the front end of the barrel is open and a viscous material containing cartridge or the like can be snap-fit in position where the front end is open. With such a construction, it is possible for a snap-fitted cartridge to accidentally and undesirably be ejected from the barrel through the open lower portion of the barrel.

U.S. Pat. No. 5,125,836 to Dragan et al. discloses a viscous material extruder with a slot located a full circumference front end for receiving a nozzle of a cartridge. A shoulder extending substantially the full circumference of the front end holds the cartridge. However, the slot remains open and it is possible that a cartridge or the like could accidentally and undesirably become dislodged and/or ejected through the slot.

A number of devices have been contemplated to encircle a cartridge mounted in a syringe type dispenser. For example, U.S. Pat. No. 4,295,828 to Rudler discloses a viscous material extruder with a front end of the barrel provided with a hinging section for loading and locking a cartridge in place at the front end of the barrel. However, the Rudler device requires a number of relatively complex parts that can increase the cost of manufacturing the syringe type dispenser.

SUMMARY OF THE INVENTION

It is an object of this invention to overcome deficiencies and limitations of the known viscous material syringe dispensers.

It is a further object of this invention to provide a viscous material syringe dispenser having a simple and economical mechanism in which a capule can be inserted into the viscous material syringe dispenser and then locked into place where the capule is supported about the entire circumference thereof.

The above and other objects of this invention are achieved by a viscous material dispenser that is adapted to lock into place a capule or the like for containing the viscous material. The capule and the viscous material contained therein can be inserted into a syringe type dispenser for the controlled application of the viscous material. The dispenser includes a locking mechanism mounted on the syringe type dispenser to securely retain the capule within the syringe type dispenser while the viscous material is being applied from the syringe type dispenser. The locking mechanism can be positioned so that it rotates around and over the outer circumference of the barrel of the syringe type dispenser. The locking mechanism can be rotated to an open position from which a capule can be inserted or removed from the syringe type dispenser and a closed position from which a capule is locked into position for dispensing.

BRIEF DESCRIPTION OF THE DRAWINGS

This invention will become apparent from the following description of embodiments of the invention taken in conjunction with the accompanying drawings, in which.

DESCRIPTION OF THE PREFERRED EMBODIMENTS

Figure 1:
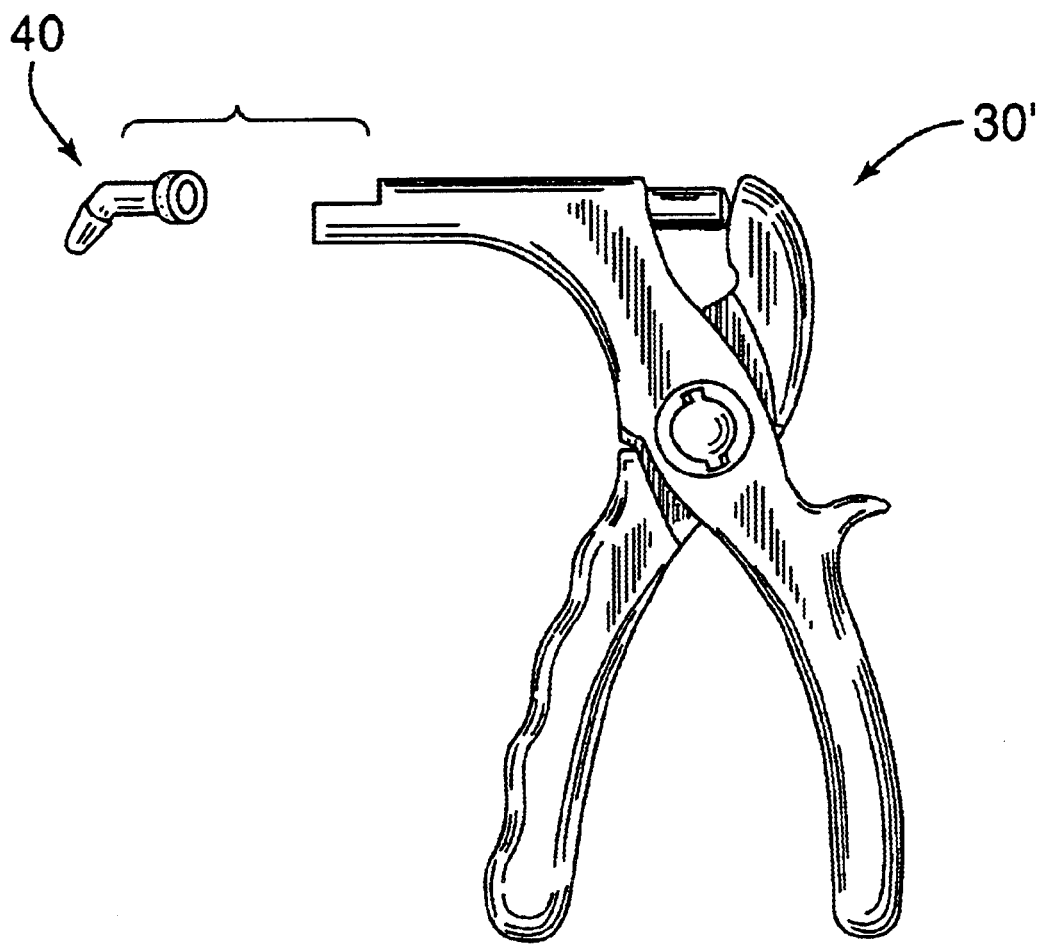
FIG. 1 is a side view of a conventional viscous material dispenser, along with a separate capule.
Figure 2:
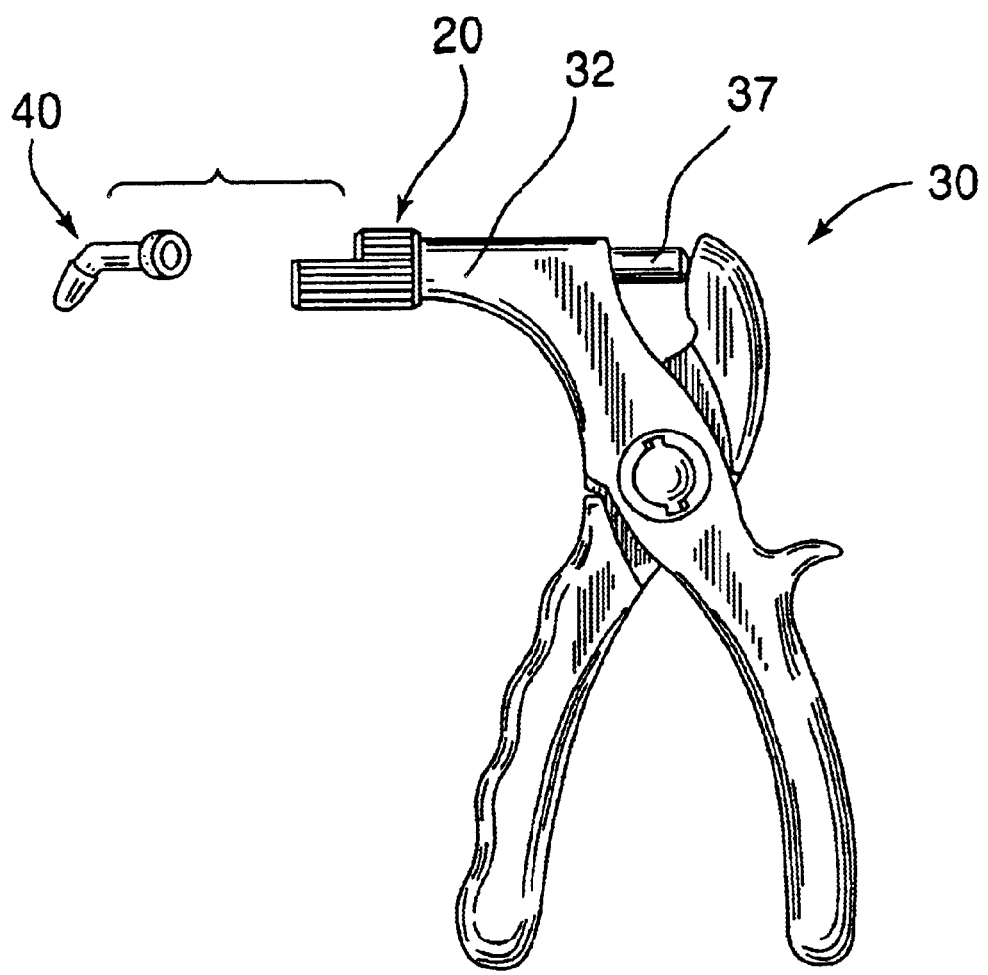
FIG. 2 is a side view of an embodiment of a viscous material dispenser having a capule lock, in accordance with embodiments of this invention, along with a capule.
Figure 3:
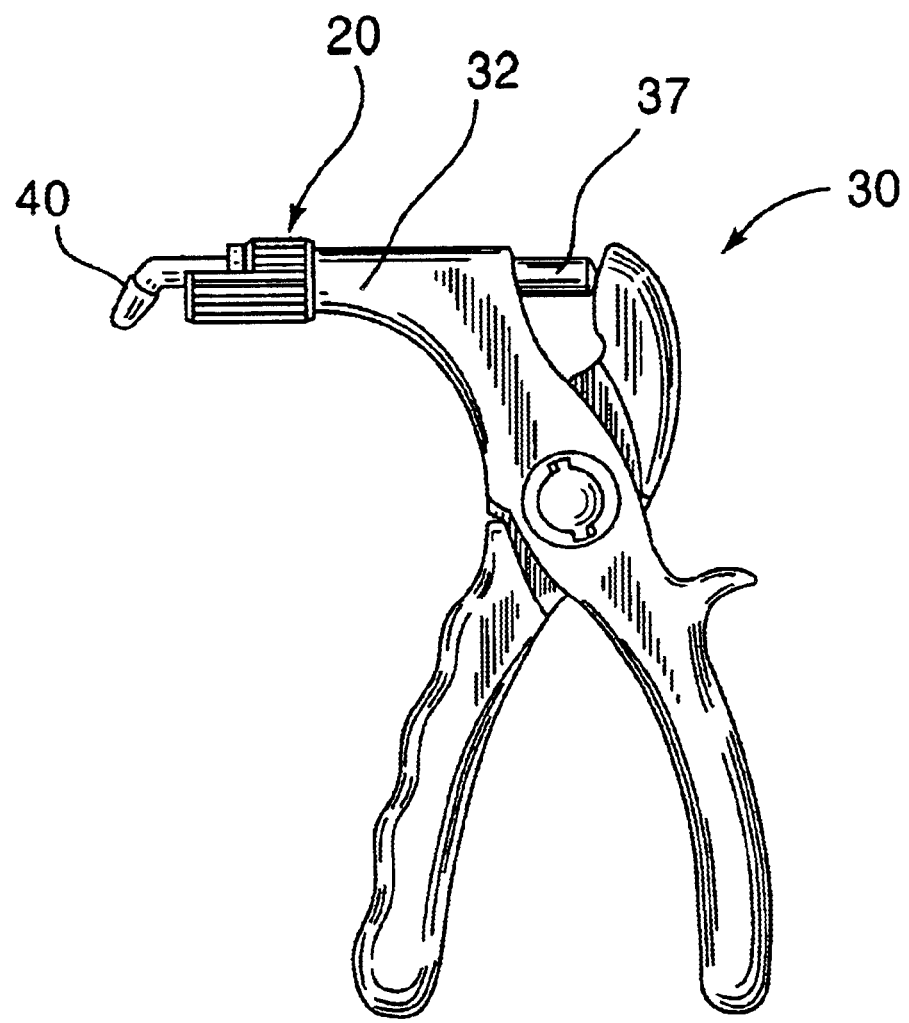
FIG. 3 is a side view of an embodiment of a portion of a viscous material dispenser having a capule lock shown with a capule unlocked and ready to be locked in place in accordance with embodiments of this invention.
Figure 4:
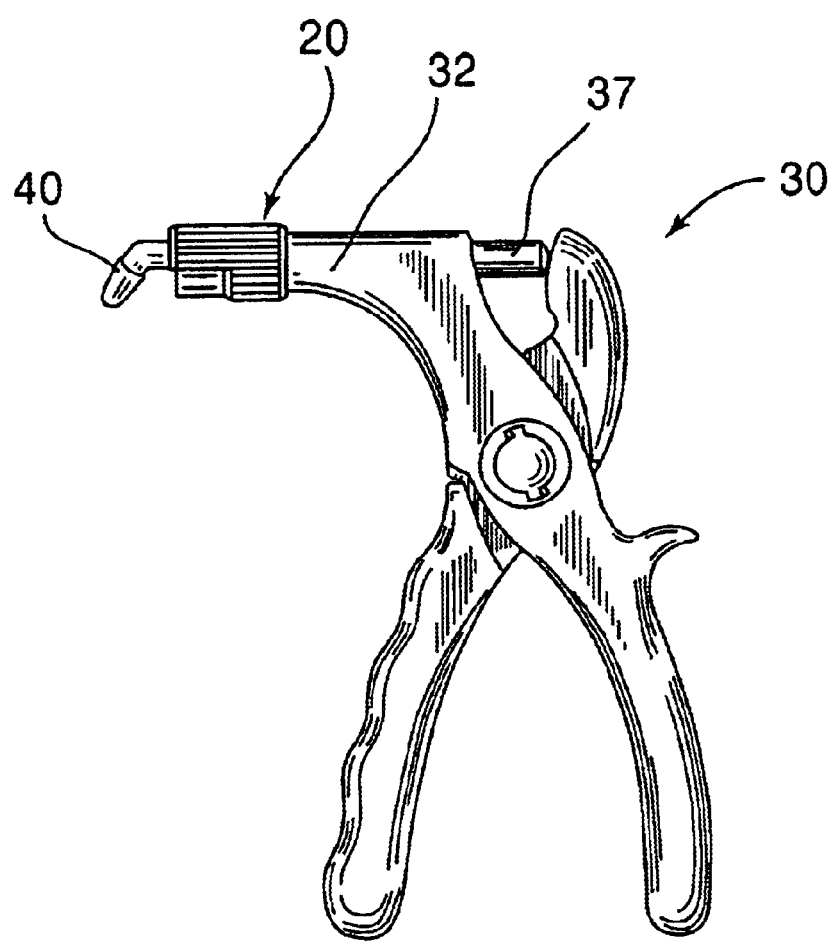
FIG. 4 is a side view of an embodiment of a portion of a viscous material dispenser having a capule lock shown with a capule locked in place in accordance with embodiments of this invention.
Figure 5:
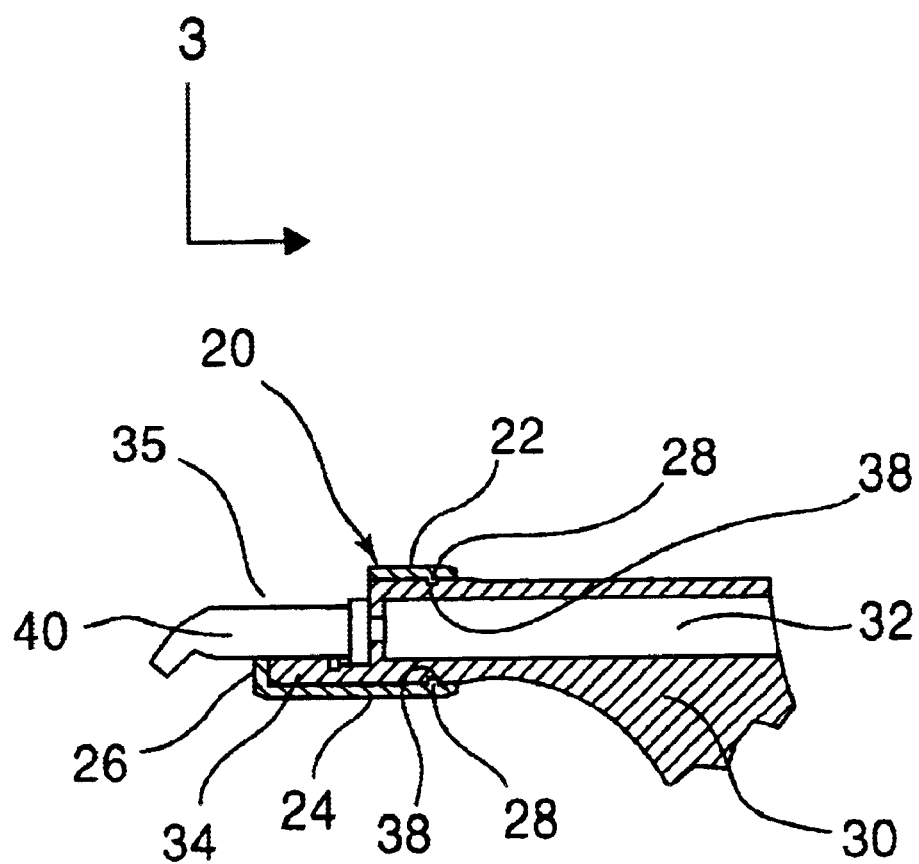
FIG. 5 is a cross-sectional side view of the embodiment of FIG. 3 taken from perspective 3—3.
Figure 6:
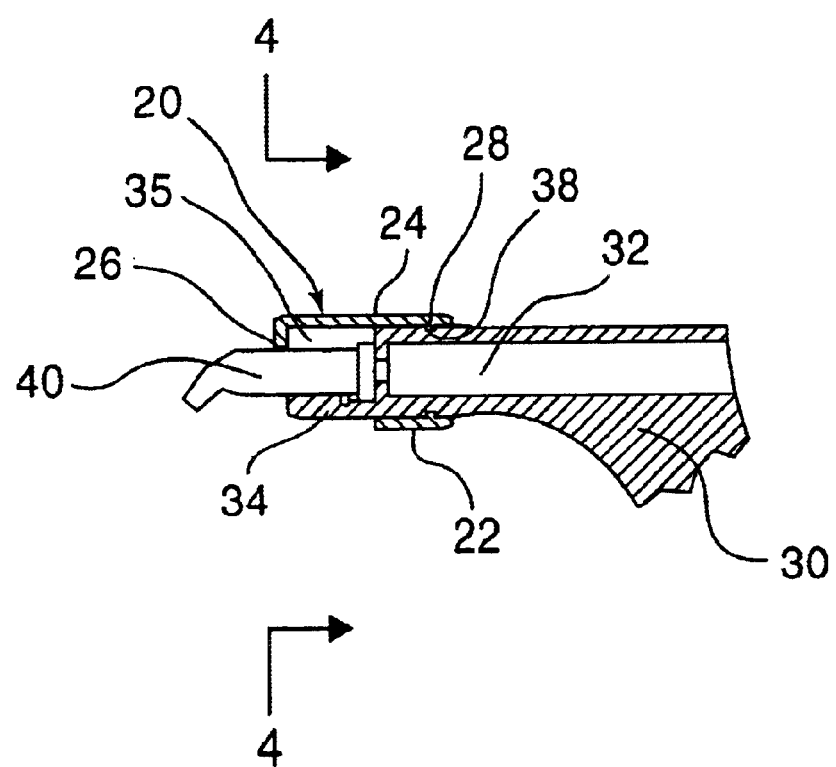
FIG. 6 is an cross-sectional side view of the embodiment of FIG. 4 taken from perspective 4—4.

Referring now to FIGS. 2–6, there is shown viscous material dispenser 30 for the application of a viscous dental material contained within a viscous material container such as, and for example, a capule, cartridge or capsule, for example capule 40, after insertion of the capule 40 into the end portion of a barrel 32 of a syringe 30. The capule, cartridge or capsule 40 can be inserted into the syringe 30 in a similar manner to insertion in the conventional device of FIG. 1.

The end portion 34 of a barrel 32 of the dispenser 30 extends only partially circumferentially, leaving an opening 35, thus such that the capule 40 can be inserted through the opening 35 into and against a closed portion 34, which acts as a slot to hold the capule 40.

The viscous material dispenser 30 of this invention has a capule, capsule or cartridge lock, for example capule lock, 20, that is positioned at the end portion 34 of the barrel 32. The lock 20 is fixed to the portion 34 such that the lock is able to rotatably slide over and around the outer circumference of the portion 34 and over and around the opening 35. The portion 24 of the lock 20 closest to the dispensing end of the barrel 32 only extends around part of the circumference of the barrel 32. In embodiments, the portion 22 of the lock 20 furthest from the dispensing end can extend completely around the circumference of the barrel 32. A lip 26 extends from the portion of the lock closest to the dispensing end of the barrel to cover a portion of the open end of the barrel 32.

The lock 20 is adapted to rotatably slide along the outer circumference of the barrel 32 such that a portion of the lock 20 can be rotated into a position covering the open top portion 35 and can be rotated into a position covering the portion 34 where the open top portion 35 is left uncovered.

In embodiments, the lock 20 only rotates around the outer circumference of the barrel 32, and does not slide linearly along the barrel 32. This can be achieved, for example, with the barrel 32 having an engaging means, such as, and for example, a groove or recess 38 extending around the outer circumference of the barrel 32. Such an engaging means can include a radial protrusion 28 or the like on the lock 20 that fits in the recess 38 in the barrel 32 such that the lock 20 is free to slide around the circumference of the barrel 32 but prevented from sliding linearly along the barrel 32.

The apparatus of this invention can be generally applied to a wide variety of viscous materials. However, in particular, viscous material dispenser 30 may be applied to such viscous materials as dental cement, composites and fillers.

In the illustrated embodiment, the viscous material dispenser 30 is shown with an applicator tip 40 having an angled nozzle for accurate placement of the viscous material, along with a pressure ram 37.

Although embodiments of this invention have been described in detail, it will be understood that this invention is not limited to the above-described embodiments, and various modifications in construction may be made without departing from the spirit and scope of this invention and any and all equivalents thereof as defined in the following claims.

What is claimed is:

1. A viscous material dispenser that applies a viscous material from viscous material container such as a capule, cartridge or capsule, comprising:
   (a) a dispensing barrel, a dispensing end portion having an opening into which the viscous material container can be inserted and removed from the dispensing end portion of the dispensing barrel;
   (b) a lock for securely locking the viscous material container in the dispensing end portion of the dispensing barrel, the lock being rotatable around the outer circumference of said dispensing barrel, an end portion of the lock corresponding to the end portion of the dispensing barrel, said end portion having an open portion that can rotate about the dispensing end portion of the dispensing barrel such that the viscous material container can be inserted or removed from the dispensing end portion when the open portion of the lock corresponds with the opening in the dispensing end portion, and the viscous material container can be securely retained in the slot when the open portion covers the opening in the dispensing end portion of the dispensing barrel.

2. The viscous material dispenser of claim 1 wherein the viscous material dispenser includes a means for allowing the lock to slide around the outer circumference of the dispensing barrel and for preventing the lock from sliding linearly along the outside of the dispensing barrel.

3. The viscous material dispenser of claim 2 wherein the means is a recess in and around the circumference of a portion of the dispensing barrel that does not have an open portion and a corresponding tab around the inner circumference of a portion of the lock that does not have an open position.

4. The viscous material dispenser of claim 1 further comprising a ram for insertion into the dispensing barrel and exerting force against a viscous material containing capule, cartridge or capsule.

5. The viscous material dispenser of claim 1, further comprising a viscous material containing capule, cartridge or capsule inserted in said slot, wherein the open portion of the lock is in a position away from the open portion of the dispensing barrel.

6. The viscous material dispenser of claim 5 wherein the viscous material container contains a viscous dental treatment material.

7. The viscous material dispenser of claim 6 wherein said viscous dental treatment material is a composite material or a dental cement.

8. A method of treating a dental patient in need of such treatment, comprising utilizing the viscous material dispenser of claim 7 to dispense the viscous dental material to a tooth or to the teeth of the dental patient.

9. The viscous material dispenser of claim 1, further comprising a viscous material container, selected from a capule, a cartridge or a capsule, inserted in said means for holding and locked into position by said means for locking.

10. The viscous material dispenser of claim 9 wherein the viscous material containing capule, cartridge or capsule contains a viscous dental treatment material.

11. The viscous material dispenser of claim 10 wherein said viscous dental treatment material is a composite material or a dental cement.

12. A method of treating a dental patient in need of such treatment, comprising utilizing the viscous material dispenser of claim 10 to dispense the viscous dental treatment material to a tooth or to the teeth of the dental patient.

13. A viscous material dispenser that applies a viscous material from a container such as a capule, cartridge or capsule, comprising:
   (a) a means for holding the viscous material container in a barrel of the viscous material dispenser;
   (b) a means for locking a viscous material container in the means for holding the viscous material container, said means for locking being rotatably displaceable only around the outer circumference of the barrel of the viscous material dispenser wherein the viscous material container can be inserted or removed from the means for holding when the means for locking is in a first position and viscous material container can be securely retained in the means for holding when the means for locking is in a second position.

14. The viscous material dispenser of claim 13 wherein the viscous material dispenser includes a means for allowing the lock to rotate around the outer circumference of the barrel and for preventing the means for locking from sliding linearly along the barrel.

15. The viscous material dispenser of claim 14 wherein the means for allowing is a recess in and around the outer circumference of a portion of the barrel and a corresponding tab on the means for locking.

16. The viscous material dispenser of claim 14 further comprising a means for exerting force against the viscous material container.

* * * * *